US005912308A

United States Patent [19]

Das et al.

[11] Patent Number: 5,912,308

[45] Date of Patent: Jun. 15, 1999

[54] MULTIFUNCTIONAL CYANATE ESTER AND EPOXY BLENDS

[75] Inventors: Sajal Das, Basking Ridge; Geraldine Shu-Chuin Su, Parsippany, both of N.J.

[73] Assignee: AlliedSignal Inc., Morristown, N.J.

[21] Appl. No.: 08/347,017

[22] Filed: Nov. 30, 1994

[51] Int. Cl.[6] .......... C08F 283/00

[52] U.S. Cl. .......... 525/480; 525/481; 525/504; 525/523; 525/528

[58] Field of Search .......... 525/480, 481, 525/504, 523, 528

[56] References Cited

U.S. PATENT DOCUMENTS

| | | | |
|---|---|---|---|
| 2,806,016 | 9/1957 | Schwarzer | 260/47 |
| 2,921,037 | 1/1960 | Andres et al. | 260/2 |
| 3,562,214 | 2/1971 | Kubens et al. | 260/47 |
| 4,311,753 | 1/1982 | Pucci | 428/251 |
| 4,477,629 | 10/1984 | Hefner, Jr. | 525/113 |
| 4,487,915 | 12/1984 | Hefner, Jr. | 528/96 |
| 4,506,063 | 3/1985 | Hefner, Jr. | 523/98 |
| 4,533,727 | 8/1985 | Gaku et al. | 525/523 |
| 4,544,704 | 10/1985 | Hefner, Jr. | 525/108 |
| 4,546,131 | 10/1985 | Hefner, Jr. | 523/466 |
| 4,612,359 | 9/1986 | Hefner, Jr. | 528/97 |
| 4,831,086 | 5/1989 | Das et al. | 525/480 |
| 4,920,159 | 4/1990 | Das et al. | 523/153 |
| 4,970,276 | 11/1990 | Das et al. | 525/504 |
| 4,978,727 | 12/1990 | Das et al. | 525/504 |
| 5,043,214 | 8/1991 | Das et al. | 525/480 |
| 5,124,414 | 6/1992 | Sajal et al. | 525/504 |
| 5,126,412 | 6/1992 | Das et al. | 525/504 |
| 5,130,385 | 7/1992 | Das et al. | 525/504 |
| 5,194,331 | 3/1993 | Das et al. | 525/480 |
| 5,244,732 | 9/1993 | Brandon et al. | 428/375 |

FOREIGN PATENT DOCUMENTS

| | | | |
|---|---|---|---|
| 0411834 | 2/1991 | European Pat. Off. | 528/103 |
| 40 22 255 A1 | 1/1991 | Germany . | |
| 290 844 A5 | 6/1991 | Germany . | |
| 41 25 420 A1 | 2/1993 | Germany . | |
| 42 24 835 A1 | 2/1994 | Germany . | |
| WO 87/04443 | 7/1987 | WIPO . | |

OTHER PUBLICATIONS

"Co–Reaction of Epoxide and Cyanate Resins"–D.A. Shimp, et al., presented at 33rd Int'l. SAMPE Symposium & Exhibition, pp. 1 to 13, (Anaheim, CA, Mar. 7–10, 1988).

"Networks from Cyanates and Glycidyl Ethers Reactions, Network Structure and Properties", G. Meyer, et al., Polymeric Materials Science and Engineering Fall Meeting 1994, vol. 71, Washington, DC, United States, Aug., 1994, pp. 797 & 798.

"AroCy® Cyanate Ester Resins", Chemistry, Properties and Applications, brochure by D.A. Shimp, et al., Rhŏne–Poulenc Inc., Third Edition, May 1991, pp. i, & 26.

"Formulating with DOW Epoxy Resins, Electrical Laminates," brochure by Dow Plastics, pp. 2–8 (Feb. 1990).

Lee et al. "Handbook of Epoxy Resins", pp. 2–1 to 2–27, 1982 Reissue, McGraw Hill.

*Primary Examiner*—Randy Gulakowski
*Attorney, Agent, or Firm*—Fisher, Christen & Sabol

[57] ABSTRACT

A curable resin blend including a multifunctional phenolic cyanate/phenolic triazine copolymer; and an epoxy resin, and articles manufactured therefrom. The cured resin blend possesses a high glass transition temperature, flexural strength, elongation, flexural modulus, compressive strength, and compressive modulus properties as well as low moisture absorption properties. The cured blend is suitable for making laminates, coatings, composites, and molds such as via resin transfer molding, compression molding, and the like.

31 Claims, No Drawings

MULTIFUNCTIONAL CYANATE ESTER AND EPOXY BLENDS

BACKGROUND OF THE INVENTION

1. Field of the Invention

This invention relates to certain novel blends of phenolic cyanate-phenolic triazine copolymers and epoxy resins, as well as to articles prepared from said blends. More particularly, this invention relates to such blends which have improved properties.

2. Prior Art

Phenolic resins are a class of synthetic materials which greatly vary in molecular structure. Therefore, a multitude of applications for these products exists as a result of the array of physical properties that arise from the synthetic options. However, phenolics disadvantageously exhibit less than desirable thermal oxidative stability and produce an extensive, uncontrollable amount of volatile by-products during crosslinking.

In order to obviate certain of the disadvantages attendant to phenolics, U.S. Pat. No. 4,970,276 proposed a modified multifunctional phenolic cyanate/phenolic triazine copolymer ("PT resin") which had greater oxidative, mechanical, and thermal stability as compared to conventional phenolic resins, and did not produce volatile by-products during crosslinking. Further, these PT resins possessed better elongation properties and higher glass transition temperatures than the conventional phenolic resins. Additional examples of such PT resins are described in U.S. Pat. Nos. 4,970,276, 4,978,727, and 5,126,412.

Another approach for producing thermosettable blends having improved mechanical properties is by blending dicyanate esters with epoxy resins as disclosed in U.S. Pat. Nos. 4,612,359, 4,506,603, 4,477,629, 4,546,131, 4,487,915, 3,562,214 and in Shimp, et al., "Co-Reaction of Epoxide and Cyanate Resins," 33rd Int'l SAMPE Symposium and Exhibition 1–13 (California Mar. 7–10, 1988) and Shimp, AroCy® Cyanate Ester Resins Chemistry, Properties & Applications, (3rd Ed. May, 1991). These blends have been useful in the production of base materials for printed circuits as disclosed in Patent Nos. DE 4022255, DD 290844, DE 4125420, and DE 4224835.

Although the above inventions provide thermosettable resin blends which, when cured, possess excellent thermal stability and mechanical properties, there is room for additional improvement in the overall mechanical properties, especially in glass transition temperature, as well as in water absorption.

It would be desirable to provide a thermosettable resin blend which, when cured, is superior to prior art phenolic resins and dicyanate blends in one or more of the properties selected from glass transition temperature, flexural strength, flexural modulus, elongation, and water absorption.

SUMMARY OF THE INVENTION

In accordance with this invention, there is provided a blend comprising:

a) a multifunctional phenolic cyanate/phenolic triazine copolymer comprising three or more phenolic moieties of formula I.:

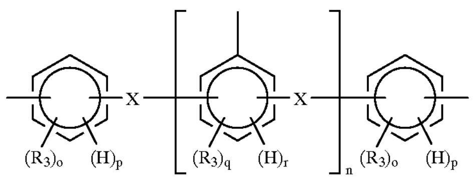

linked by way of at least one of open valences to one or more triazine moieties of the formula II:

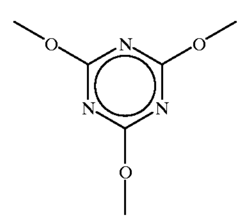

and wherein the remainder of the open valences of said phenolic moieties are substituted with —OH, —OCN, or other triazine moieties, provided that at least one of said remaining open valences is substituted with a —OCN moiety; wherein:

n is a positive whole number equal to or greater than 1;

q and r are the same or different at each occurrence and are whole numbers from 0 to 3 with the proviso that the sum of q and r at each occurrence is equal to 3;

o and p are the same or different at each occurrence and are whole numbers from 0 to 4, with the proviso that the sum of o and p is equal to 4;

—X— is a divalent organic radical; and $R_3$ is the same or different at each occurrence and is a substituent other than hydrogen which is unreactive under conditions necessary to completely cure the copolymer; and b) an epoxy resin.

Another aspect of this invention pertains to the article resulting from curing the aforementioned blend with a curing quantity of a curing agent, catalyst or mixture of curing agent and catalyst therefore.

The blend of this invention and the products resulting therefrom exhibit one or more beneficial properties, such as improved glass transition temperature and water absorption.

DESCRIPTION OF THE PREFERRED EMBODIMENTS

Component a of the present invention includes multifunctional phenolic cyanate/phenolic triazine copolymer resins or "PT resins" having at least three phenolic moieties of the Formula I linked by at least one of said open valences to one or more triazine moieties of the Formula II. The remainder of said open valences being substituted with —OCN, —OH or other triazine moieties, provided that at least one of said remaining open valences is substituted with a —OCN group, wherein $R_3$, n, q, r, o, and X are as described above.

In the structure of Formula I, $R_3$ is an inert substituent. Illustrative of suitable $R_3$ groups are such inert substituents as halogen, trihalomethyl, alkyl, alkoxy, phenyl, and the like.

In the structure of Formula I, —X— is a divalent organic radical. Illustrative of suitable —X— groups are alkylene such as methylene, ethylmethylene, 2-ethylpentylmethylene, methylmethylene, isopropylmethylene, isobutylmethylene, pentylmethylene, furylmethylene, and the like; arylenes such as 1,3-benzenedimethylene, phenylmethylene, 1,4-benzenedimethylene, 2,2-bis-(4-phenylene)methane, 4,4-diphenylene dimethylenethane and the like; and cycloalkylenes such as cyclohexylene, cyclooctylene, 1,3-cyclohexanedimethylene, and the like.

In the preferred embodiments of the invention:

—X— is a substituted or unsubstituted methylene or 1,4-phenyldimethylene wherein permissible substituents are alkyl or furyl;

q and r are the same or different at each occurrence and are positive whole numbers from 0 to 3, with the proviso that the sum of 0 and r is 3;

$R_3$ is alkyl;

n is from 1 to about 20; and o and p are the same or different at each occurrence and are positive whole numbers from 0 to 4, with the proviso that the sum of o and p is 4;

wherein up to about 30 mole percent of the phenyl moieties of said copolymer are substituted with said triazine moieties, up to about 90 mole percent of said phenyl moieties are substituted with —OH groups and up to about 90 mole percent of said phenyl moieties are substituted with —OCN groups, said mole percent based on the total moles of phenyl groups in said copolymer. Unless indicated otherwise, all references herein are in terms of weight percent.

Amongst the preferred embodiments of the invention, particularly preferred are those embodiments of the invention in which:

from about 2 to about 25 mole percent of said phenyl groups of the PT resin are substituted with triazine moieties, from about 40 to about 90 mole percent of said phenyl groups are substituted with —OCN groups and from about 2 to about 50 mole percent of said phenyl groups are substituted with —OH groups, said mole percent based on the total moles of phenyl group in said copolymer;

—X— is methylene, methylene substituted with alkyl having from about 1 to about 10 carbon atoms, halogen or furfuryl, or xylene;

$R_3$ is methyl or ethyl;

o is 0 or 1;

n is from about 1 to about 10;

q is 0 or 1;

r is 2 or 3;

p is 3 or 4.

Amongst these particularly preferred embodiments, most preferred are those embodiments wherein:

n is 3 to about 10;

from about 5 to about 20 mole percent of the phenyl groups of the phenyl triazine/phenyl cyanate copolymer are substituted with —OCN groups and from about 5 to about 20 mole percent of said phenyl groups are substituted with —OH groups; said mole percent based on the total moles of phenyl groups in said copolymer;

q is 0;

o is 0;

X is a moiety of the formula: $—CH_2—$, $—CF_2—$,

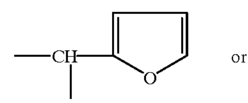

or

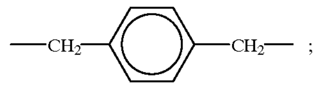

;

r is 3; and p is 4.

Especially good results are obtained in the practice of this invention where from about 10 to about 20 mole percent of the phenyl groups in the PT resin are substituted with triazine moieties, from about 10 to about 20 mole percent of said phenyl groups are substituted with —OH groups and from about 60 to about 80 mole percent of said phenyl groups are substituted with —OCN groups, said mole percent based on the total moles of phenyl groups in said copolymer.

These especially preferred copolymers are preferably linear copolymers having recurring units of the Formula III:

III.

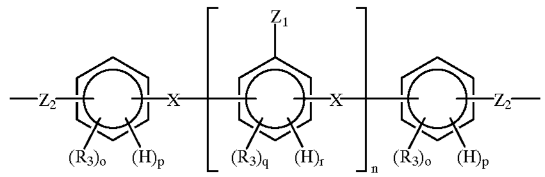

wherein $R_3$, o, p, q, r, —X—, and n are as described above and wherein:

$Z_1$ is —OH and —OCN;

$Z_2$ is a trivalent triazine moiety;

with the proviso that from about 10 to about 20 mole percent of the phenyl groups of the copolymer are substituted with trivalent triazine moieties, from about 70 to about 75 mole percent of phenyl groups as substituted with —OCN groups, and from about 10 to about 20 mole percent of the phenyl groups are substituted with —OH groups, said mole percent based on the total moles of phenyl groups in the copolymer.

Suitable materials which can be employed in the preparation of the phenolic cyanate resin precursor to the PT resin of component a include base phenolic salts of Formula IV:

IV.

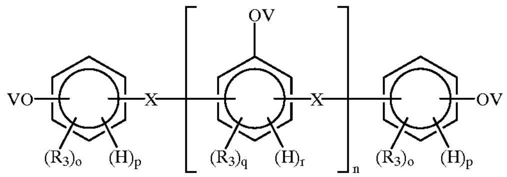

wherein $R_3$, q, r, o, p, n, $Z_1$, and X are as described above, and V is hydrogen or cation of an organic or inorganic base which is formed by reaction between said base and the protons of a phenolic to form the corresponding basic salt, wherein the mole ratio of cations to hydrogen are sufficient to form the desired mole percent of —OCN groups in the desired phenolic cyanate.

These base phenolic salts react with cyanogen halides via a nucleophilic displacement reaction in order to produce the phenolic cyanate resin precursor used in the preparation of the PT resins of component a, details of which are disclosed in U.S. Pat. No. 4,970,276, which is incorporated by reference herein.

PT resins suitable for use in component a of the blend of the present invention may be prepared by the known method of controlled "polycyclotrimerization" of the phenolic cyanate precursor having formula V:

V.

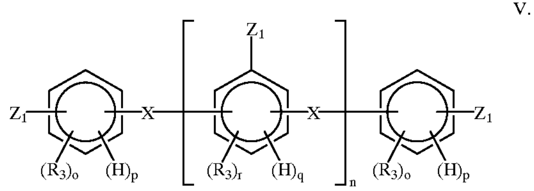

to the extent necessary to form the desired mole percent of trivalent triazine moieties, wherein $R_3$, n, q, r, o, p, $Z_1$, and X are as described above, provided that the amount of $Z_1$ group which are —OCN is sufficient to provide the desired mole percent of triazine moieties and —OCN moieties in the desired copolymer. Details of the method for PT resin production are also described in U.S. Pat. No. 4,970,276.

Suitable epoxy resins for blending with the PT resin include bisphenol-A-based epoxy resins, halogenated epoxy resins, epoxy novolac resins, polyglycol epoxy resins, and mixtures and copolymers thereof. Illustrative of suitable bisphenol-A-based epoxy resins include compounds of the following formula:

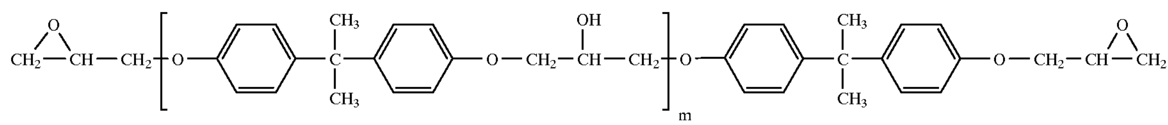

wherein m is from about 0.1 to about 1, preferably about 0.1 to about 0.2.

Illustrative of suitable epoxy novolac resins include compounds of the following formula:

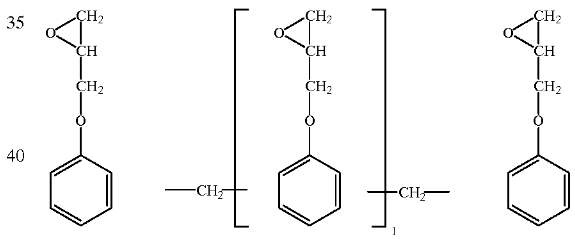

wherein I is from about 0.1 to about 2, preferably about 0.1 to about 0.3.

Suitable halogenated epoxy resins include those epoxies substituted with chlorine, bromine, fluorine, and mixtures thereof. Illustrative of suitable brominated epoxy resins include compounds of the following formula:

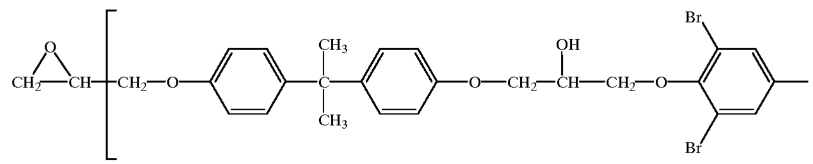

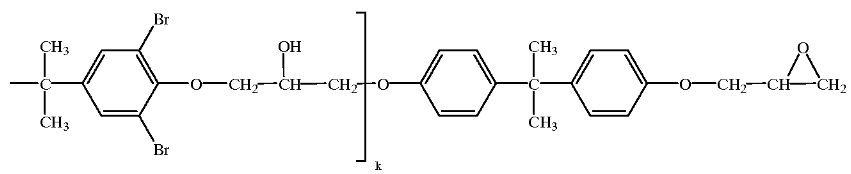

wherein k is from about 2 to about 3, preferably about 2 to about 2.5. Illustrative of suitable polyglycol epoxy resins include compounds of the following formula:

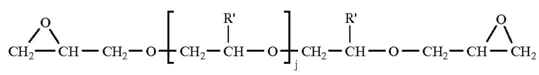

wherein j is from about 1 to about 2, preferably about 1.9 to about 2.0, and R' is a hydrogen or an organic group, such as an alkyl group having from about 1 to about 5 carbons. These epoxy resins can be obtained from commercial sources, e.g. from the Dow Chemical Company.

Other suitable epoxy resins include multifunctional epoxy resins, such as tetra- and tri-functional epoxy resins, which may used alone, or mixed or copolymerized with the above-described epoxy resins. As used herein, "multifunctional epoxy resin" means a resin which may contain greater than about 1 to about 4, preferably 3 to about 4 epoxy groups, more preferably 4 epoxy groups. Illustrative of such tetra-functional and tri-functional multifunctional epoxy resins are

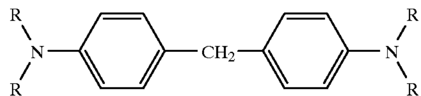

wherein R is

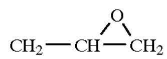

and

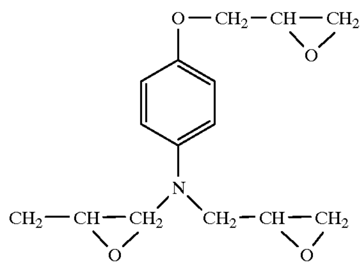

respectfully, which can be obtained from commercial sources, e.g. from Ciba-Geigy Corporation under the tradename "Araldite".

In a preferred embodiment, an epoxy having, based upon the total weight of the epoxy resin, from about 15 percent to about 45 percent, preferably about 8 percent to about 12 percent, bromination is employed. Unless indicated otherwise, all references herein are with respect to weight percent. As the amount of brominated epoxy resin in the blend of the present invention is increased, various properties, such as adhesion and glass transition temperature ("Tg") also increase.

In an alternative embodiment wherein a blend having a low viscosity is desired, the incorporation of a polyglycol epoxy resin is preferred.

The blend of the present invention includes a mixture of, based upon the total weight of the blend, from about 5 to about 95 percent, preferably from about 15 to about 50 percent, and more preferably about 25 to about 30 percent PT resin with from about 5 to about 95 percent, preferably about 25 to about 70 percent, epoxy resin.

The blend of the present invention may optionally contain, based upon the total weight of the blend, from about 0 to about 20, preferably about 3 to about 10 percent, of a multifunctional epoxy resin in addition to the amount of epoxy resin or resins employed in component b. Examples of suitable multifunctional epoxy resins include those described above. When a blend having high Tg and adhesion properties is desired, it is preferred that such multifunctional epoxy resins are used as a third component in the blend of the present invention.

The blend of the present invention may also optionally contain a catalyst for the purpose of increasing the cure rate of the blend. The amount of the catalyst employed depends largely on the type of the catalyst, the curing conditions, and/or the use of the final cured product. Usually, the blend of the present invention contains, based upon the total weight of the blend, from about 0.01 percent to about 0.2 percent, preferably 0.08 percent to about 0.11 percent of a catalyst.

Suitable catalysts employed herein are the primary catalysts and/or the organic catalysts or "curing agents". Illustrative of the primary catalysts include, for example, transition metal salts of aliphatic and aromatic carboxylic acids, nitrogen and phosphorus compounds. Particularly suitable catalysts include, for example, lead naphthenate; manganese naphthenate; manganese octoate; manganic acetylacetonate; cobalt octoate; cobalt naphthenate; cobalt acetylacetonate; zinc octoate; zinc naphthenate; zinc acetylacetonate; copper acetylacetonate; cupric naphthenate; nickel acetylacetonate; titanyl acetylacetonate; ferric octoate; tin octoate; diazobicyclo[2.2.2.]octane; catechol; 1,3-dimethyl-3-phenylurea; mixtures thereof and the like. Manganese octoate is most preferred. These catalysts are obtainable from commercial sources, e.g. from Aldrich Chemical Company, Inc., and Pfaltz & Bauer, Inc.

Other suitable catalysts include organic catalysts or curing agents, such as alkyl phenols, imidazoles, and mixtures thereof. These organic catalysts or curing agents are employed for the purpose of further accerlating the cure, and may be used alone or in combination with the above-mentioned metal catalysts. Preferable organic catalysts may be selected from the group consisting of nonylphenol, 1-methylimidazol, 2-ethyl-4-methylimidazol, 2-phenylimidazole ("2-MI"), with 2-MI being most preferred. These organic catalysts are also obtainable from commercial sources, e.g. from Aldrich Chemical Company, Inc.

In a preferred embodiment, based upon the total weight of the blend, from about 0.025% to about 0.06% of manganese octoate with about 0.06% to about 0.07% 2-MI may be employed.

If desired, the blend, i.e. the PT resin and/or epoxy resin component, can be blended with other compounds such as, for example, solvents, fillers, mold release agents, pigments, dyes, flow modifiers, combinations thereof and the like. Examples of such compounds are described in U.S. Pat. No. 4,496,695, which is incorporated by reference herein.

Suitable such solvents include, for example, aromatic hydrocarbons, ketones halogenated hydrocarbons, combinations thereof and the like. Particularly suitable solvents include, for example, dimethylformamide, tetrahydrofuran, acetone, 1-methyl-2-pyrrolidinone, methylethylketone, methylene chloride, combinations thereof and the like.

The PT resin and/or epoxy resin may contain fillers for use in where the structural strength and integrity of a structure has to be maintained, and for other purposes known to those of skill in the art. Any suitable filler known to those of skill in the art may be used. Such fillers may be selected from a wide variety of organic and inorganic materials such as polymers, minerals, metals, metal oxides, siliceous materials, and metal salts. Illustrative of useful fillers are kevlar fibers, rock-wool, slag wool, fiber glass, phenolic fibers, aramide, boron, and carbon fibers, as well as plate like, fibrous and particulate forms of alumna, brass powder, aluminum hydrates, iron oxide, feldspar, lead oxides, asbestos, talc, barytles, calcium carbonates, clay, carbon black, quartz, novaculite, and other forms of silica, koalinite, aluminum silicate bentonite, garnet, mica, saponite, beidelite, calcium oxide, fused silica, calcium hydroxide, synthetic fibers such as paper, pulp, wood flour, cotton, linter and polyimide fibers, and the like. Other useful fillers include thermoplastic polymers, as for example, polyesters, polyimides, polyamides, polysulfones, polyaramids, polyester carbonates, ployphenylene ether, polyethersulfones, polyethylene, polypropylene, polycarbonates, polyetherimides, polysulfides, polyacrylates, polyvinyls and the like. Methods for producing reinforced and/or filled blends include melt blending, extrusion and molding processes, simple mixing and dispersion of both materials in suitable medium by methods known in the art.

For coloring purposes, a curable resin blend of this invention may include white pigments such as titanium dioxide, and coloring pigments or various organic dyes and pigments, such as lead yellow, carbon black, iron black, molybdenium red, prussian blue, navy blue, cadmium yellow, and cadmium red.

The curable resin blends of the present invention may be prepared by either a wet process or a dry process, both of which are conventionally known in the art. Choice of the process is determined by the proportion of components and final use of the blend.

In the wet process, each component is individually dissolved in a solvent, then all of the components are blended so as to obtain a curable resin blend having the desired proportion. Alternatively, at least one of the components is dissolved in a solvent, and the other components are added thereto. In view of the high viscosity of both the PT resin and epoxy, it is preferred that, when selecting the latter embodiment, at least these two components are initially dissolved in a solvent before other components are added thereto. Otherwise, it may be necessary to heat the PT resin-epoxy mixture to temperatures ranging from about 65° C. to about 75° C. in order to lower the viscosity and improve the mixing thereof, and thus reduce the likelihood of non-uniformities in the end product.

The blends prepared according to the wet process contain a solvent or solvents. The solvent may be removed by heating the blend or by keeping the blend under a reduced pressure.

Solvents suitable for dissolving the components employed in the wet process include, for example, ketones, such as acetone, methyl ethyl ketone, and the like, as well as tetrahydrofuran, methylene chloride, dimethylformamide,1-methyl-2-pyrrolidinone, and the like.

According to the dry process, the PT resin and epoxy resin components are continuously mixed via conventional means at temperatures of about 65° C. to about 75° C. until homogeneous. An effective amount of a solution comprised of from about 15 to about 25 percent, based upon the total weight of the solution, of catalyst predissolved in an alkyl phenol solvent, such as nonylphenol, dodecylphenol, o-cresol, 2-sec.butylphenol and 2,6-dinonylphenol, most preferably nonylphenol, may optionally be added thereto such that the amount of catalyst in the homogenously blended blend is from about 0.06 to about 0.07 percent, based upon the total weight of the blend. The resulting blend is continuously stirred for about 20 minutes to about 1 hour until homogeneous.

Further details regarding both the wet process and the dry process are described in "Formulating with Dow Epoxy resins Electrical Laminates" by the Dow Chemical Company (February 1990).

The method of curing the resin blend of this invention is not restricted in particular. Usually it is performed by heating. Generally a temperature of about 18° C. to about 400° C., preferably a temperature of about 100° C. to about 300° C., is selected. The time required for curing differs depending upon the form in which the resin blend of this invention is used, i.e. depending upon whether it is a thin film, or a relatively thick molded article or laminate. Usually, a period sufficient for curing the resin may be selected from the range of from about 1 hour to about 2 hours. When the resin blend of this invention is to be used in molded articles, such as those produced via resin transfer molding, compression molding, injection molding, and the like, laminates or bonded structures, it is desirable to apply pressure during the heat curing mentioned above.

Other curing methods involve use of microwave, radio frequency, ionizing radiation, electron beams from various types of accelerators, gamma-rays from isotopes such as cobalt 60, sunlight, and active energy, for example, light radiated from a light source such as a tungsten lamp, or a low-pressure or high-pressure mercury lamp. In the case of photocuring, the resin blend of this invention may contain up to 5 percent, based upon the total weight of the blend, of a known photosensitizer, for example, an organic carbonyl compound such as benzoin, benzoin methyl ether, benzathrone, anthraquinone and benzophenone, or a combination of a sensitizing dye such as eosine, erythrosine or acridine with an amine. Such a photocurable resin blend containing a photosensitizer is effective in coating applications.

The blends of the present invention are preferably employed to prepare articles including, but not limited to, composites and laminates, i.e. electrical laminates such as printed circuit boards. In preparing the boards, a fibrous substrate or reinforcing material is impregnated and laminated with one or more plies, preferably about 4 to about 8 plies, of the blend of the present invention. Conventional coating equipment can be employed. Subsequent to coating, the impregnated substrate is cured at a temperature of about 100° C. to about 300° C. for about 1 hour to about 2 hours to form a rigid substrate. The blends can be used to coat and/or impregnate fibrous substrates such as fiberglass, nylon, paper such as that obtainable from DuPont under the tradename "Thermount", polyimides, graphite, and the like. The substrate can be in the form of woven fabric, mat, monofilament, multifilament rovings, and the like.

The ratio of the blend of the present invention to the substrate in a prepreg may vary from, based upon the total weight of the prepregnated substrate or "prepreg", about 20:80 to about 50:50, and preferably from about 35:65 to about 40:60. As used herein "prepreg" shall refer to the substrate coated with the uncured resin blend of the present invention.

After the rigid substrate is formed, at least one ply, preferably 1 to about 2 plies, of a sheet of copper or other electrically conductive material, e.g. gold, silver, aluminum and the like, can then be laminated to the rigid substrate using laminating conditions such as pressure of about 0.34 MPa to about 2.76 MPa (about 50 to about 400 psi) and temperatures of about 50° C. to about 300° C. applied for about 30 to about 300 minutes. Then a circuit can be etched into the conductive layer using techniques well-known to form circuit boards.

The following non-limiting examples are presented to further illustrate the present invention.

The following properties of the blends produced in the Examples were determined as follows:

a) The glass transition temperatures was determined by using differential scanning calorimetry ("DSC") via the method described in Interconnecting Packaging Circuitry 2.4.25 ("1986)("IPC"), as well as by using thermal mechanical analysis ("TMA") via the method described in IPC 2.4.24.

b) The flammability was determined via the method described in the Underwriters Laboratory UL94 Flame Test.

c) The dielectric constant and dissipation factor was determined via the methods described in ASTM D-5109, respectively, using 5.1 cm by 5.1 cm by 0.07 cm (2 in. by 2 in. by 0.028 in.) specimens at 1 MHz.

d) The percent water absorption was determined via the dip in method described in IPC 2.6.2.1 at temperatures of 23° C. and 100° C., respectively, using specimens having a thickness of 0.07 cm (0.028 in.) for Examples 1–3 and Comparative Examples 1–3, and via the method described in ASTM-D570, at a temperature of 23° C. using specimens having a thickness of 0.32 cm (0.125 in.) for Examples A–C.

e) The flexural modulus was determined via the method described in ASTM-D 790, using 1.3 cm×7.6 cm×0.32 cm (0.5"×3"×0.125"") specimens.

f) The compressive strength was determined via the method described in ASTM-D695, using 0.635 cm×0.635 cm×1.905 cm (0.25"×0.25"×0.75") specimens.

The following components are employed in Examples:

Component A is a cyanate ester resin available from AlliedSignal Inc., Morristown, N.J. under the tradename "Primaset", having a molecular weight of about 480, a viscosity @ 80° C. of about 0.3 Pa.S to about 0.35 Pa.S ( 300 to 350 cps) and a gel time of 15 to 20 mins @ 200° C.

Component B is a brominated epoxy resin available from the Dow Chemical Company having an epoxide equivalent weight ("EEW") of about 425 to about 440, a bromine content of about 20 percent by weight, and a viscosity at 25° C. of about 1.5 Pa.S to about 2.5 Pa.S ( about 1500 to about 2500 cps).

Component C is a tetra functional epoxy resin available from Shell Chemical Company under the tradename "Epon 1031" having the following formula:

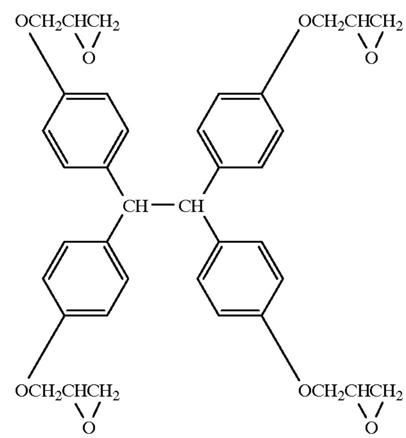

and an EEW of about 200 to about 240.

Component D is a brominated epoxy resin available from the Dow Chemical Company under the tradename "DER 592" having an EEW of about 345 to about 375, a bromine content of about 17 percent by weight, and a viscosity at 171° C. of about 0.8 Pa.S (about 800 cps).

Component E is a tetrafunctional epoxy resin available from Ciba-Geigy Corporation under the tradename "MY-720", having an EEW of about 117 to about 134 and a viscosity at 50° C. of about 8 to 18 Pa.S (about 8,000 to about 18,000 cps).

Component F is an epoxy novolac resin available from the Dow Chemical Company under the tradename "DEN 431", having an EEW of about 172 to about 179, and a viscosity at 52° C. of about 1.1 to about 1.7 Pa.S (about 1,100 to about 1,700 cps).

Component G is a liquid Bisphenol-A type epoxy resin available from the Dow Chemical Company under the tradename "DER 331", having an EEW of about 182 to about 192, an average molecular weight of about 378, a viscosity at 25° C. of about 11 to about 14 Pa.S (about 11,000 to about 14,000 cps).

Component H is a catalytic solution of manganese octoate (6 percent manganese active) in mineral spirits available from Pfaltz & Bauer, Inc.

The relative amounts of Components A, B, C, and D, as used in Examples 1–3 and Comparative Examples 1–3 are illustrated in Table I. The relative amounts of Components A, E, F, G, and H as used in Examples A, B, and C and Comparative Examples A and C are illustrated in Table II.

TABLE I

| Component % by weight | Ex 1 | Ex 2 | Ex 3 | Comp. Ex. 1 | Comp. Ex. 2 | Comp. Ex. 3 |
|---|---|---|---|---|---|---|
| A | 20.5 | 24.19 | 26.0 | | | |
| B | 59.81 | 45.44 | | 59.80 | 45.44 | |
| C | | 7.63 | 8.03 | | 7.62 | 8.03 |
| D | | | 48.9 | | | 48.84 |
| BADCY | | | | 20.49 | 24.20 | 25.96 |
| % Br by weight in blend | 12.0 | 9.1 | 8.3 | 12.0 | 9.1 | 8.3 |

TABLE II

| | Example A | Comp. Example A | Example B | Example C | Comp. Example C |
|---|---|---|---|---|---|
| Component % by weight | | | | | |
| A | 49.98 | | 49.97 | 49.97 | |
| E | 49.98 | 53 | | | |
| F | | | 49.97 | | |
| G | | | | 49.97 | 43 |
| BADCY | | 47 | | | 57 |
| H | 0.049 | | 0.054 | 0.058 | |

EXAMPLE 1

Substrate Coated With Blend of PT Resin and Brominated Epoxy Resin

About 328 parts of PT30 resin (Component A) are dissolved in about 313 parts of acetone in a 3.79 liters (1 gallon) tin can container. To this mixture are added about 957 parts of brominated epoxy resin (Component B), followed by, based upon the total weight of the mixture, about 0.03 percent of a catalytic solution of manganese octoate (6% manganese active) in mineral spirits and about 0.07% of 2-MI under room temperature conditions, then the resulting mixture is stirred for about 2 hours until homogeneous.

A glass fabric is then impregnated with the resulting mixture and cured at 177° C. (350° F.) with 1.03–1.38 MPa (150–200 psi) pressure for 15 minutes, then for about 1 hour at 220° C. (430° F.) under the same pressure conditions.

EXAMPLE 2

Substrate Coated With Blend of PT Resins Epoxy Resin With 20% Bromination, and Tetrafunctional Epoxy Resin About 395 parts by weight of PT30 resin (Component A) are dissolved in about 239 parts of acetone. To this mixture are added about 741 parts by weight of brominated epoxy resin (Component B) and about 125 parts by weight of tetrafunctional epoxy resin (Component C), followed by, based upon the total weight of the mixture, about 0.024 percent of a solution of manganese octoate (6% manganese active) in mineral spirits and 0.064% of 2-MI under room temperature conditions, then the resulting mixture is stirred for about 2 hours until homogeneous.

A glass fabric substrate is then impregnated with the resulting blend and cured in the same manner and under the same pressure conditions as described in Example 1.

EXAMPLE 3

Substrate Coated With Blend of PT Resin, Epoxy Resin With 17% Bromination, and Tetrafunctional Epoxy Resin About 390 parts by weight of a PT30 resin (Component A) is dissolved in about 255 parts of acetone. To this mixture is added about 735 parts of a brominated epoxy resin (Component D) and about 121 parts by weight of a tetrafunctional epoxy (Component C), followed by, based upon the total weight of the mixture, about 0.04% of the catalytic solution of Example 1 under room temperature conditions, then the resulting mixture is stirred for about 2 hours until homogeneous.

A glass fabric substrate is then impregnated with the resulting blend and cured in the same manner and under the same conditions described in Example 1.

Comparative Example 1

About 49.2 parts by weight of a bisphenol-A dicyanate ester (BADCY) available from Lonza Ltd. having a melting point of about 79° C., viscosity @ 80° C. is about 35 MPa.S (35 cps), specific gravity of about 1.27 @ 25° C., cyanate equivalent weight of about 139 are dissolved in a mixture of about 47.1 parts of acetone and about 143.6 parts of brominated epoxy resin (Component B). Based upon the total weight of the mixture, about 0.03% of a catalytic solution of manganese octoate (6% manganese active) in mineral spirits and 0.07% of 2MI under room temperature conditions are added thereto, then the resulting mixture is stirred for about 2 hours until homogeneous.

A glass fabric is then impregnated with the resulting blend mixture and cured at 177° C. (350° F.) for 15 minutes with about 1.38 MPa (200 psi) pressure, then for about 1 hour at 220° C. (430° F.) under the same pressure conditions.

Comparative Example 2

About 58.1 parts of bisphenol-A from Comparative Example 1 are dissolved in a mixture of about 54.4 parts by weight of acetone, about 109.1 parts of brominated epoxy polymeric material (Component B), and about 18.3 parts of tetrafunctional epoxy resin (Component C). About 0.024% by weight of a catalytic solution of manganese octoate (6% manganese active) in mineral spirits and 0.064% of 2MI by weight is added thereto under room temperature conditions, and the resulting mixture is stirred for about 2 hours until homogeneous.

A glass fabric is then impregnated with the resulting blend and cured in the same manner and under the same conditions described in Comparative Example 1.

Comparative Example 3

About 62.4 parts by weight of Bisphenol A Dicyanate ester from Comparative Example 1 is dissolved in a mixture of about 41 parts of acetone, about 117.4 parts of brominated epoxy polymeric material (component B) and about 19.3 parts of tetrafunctional epoxy resin (Component C). About 0.04% of the catalytic solution of Comparative Example 2 is added thereto, then the resulting mixture is stirred for about 2 hours until homogeneous.

A glass fabric is then impregnated with the resulting blend and cured in the same manner and under the same conditions described in Comparative Example 1.

The thermal, electrical, and moisture absorption properties of laminates described in Examples 1, 2, and 3 and Comparative Examples 1, 2, and 3 are illustrated in Table III.

TABLE III

| Property | Ex 1 | Ex 2 | Ex 3 | Comp. Ex. 1 | Comp. Ex. 2 | Comp. Ex. 3 |
|---|---|---|---|---|---|---|
| Tg (TMA), ° C. | 200 | 245 | 225 | 182 | 168–174 | 208–220 |
| Tg (DSC), ° C. | 208 | 222 | 218 | 170–172 | 183–185 | 206–207 |
| UL94 Flame Rating | V0 | V0 | V0 | V0 | V0 | V1 |
| Dielectric Constant @ 1 MHz | 4.88 | 4.32 | 4.54 | 4.29 | 4.26 | 4.30 |

TABLE III-continued

| Property | Ex 1 | Ex 2 | Ex 3 | Comp. Ex. 1 | Comp. Ex. 2 | Comp. Ex. 3 |
|---|---|---|---|---|---|---|
| Dissipation Factor @ 1 MHz | 0.0128 | 0.0150 | 0.0158 | 0.0112 | 0.0119 | 0.0139 |
| % Water Absorption | | | | | | |
| D24/23° C. | 0.25 | 0.33 | 0.37 | 0.25 | 0.35 | 0.38 |
| D24/100° C. | 0.66 | 0.99 | 0.92 | 0.89 | 1.21 | 1.49 |

It can be seen from Table III. that substrates coated with the blend of the present invention have excellent thermal, electrical, and moisture absorbance properties. In particular, the glass transition temperature and the water absorption properties possessed by the multicyanate ester-containing blend of the present invention are superior to those properties possessed by prior art compositions employing a bisphenol A dicyanate ester. Further, as the amount of multicyanate ester in the blend of the present invention is increased, the glass transition temperature and other mechanical properties will also increase.

EXAMPLE A

Blend of PT Resin With Tetrafunctional Epoxy Resin

About 202.7 parts by weight of a PT-30 resin (Component A) and about 202.7 parts of a tetrafunctional epoxy resin (Component E) are combined in a 500 ml beaker. The beaker is heated in an oil bath at ambient pressure for about 20 minutes until the temperature of the mixture is about 75° C., while the mixture contained therein is simultaneously stirred until homogeneous. About 0.2 parts of a catalytic solution (Component H) was added thereto, and the resulting mixture is stirred until the catalyst completely dissolves.

The resulting blend is poured into a 20.3 cm×17.78 cm×0.32 cm ( 8"×7"×1/8") glass mold preheated to about 80° C., which was pretreated with a silicone release agent available from Chemlease Inc. under the tradename "Chemlease 70", then the filled mold is degassed in a vacuum oven set at about 70° C. to 80° C. with about 4000 Pa vacuum pressure (30 torr). After 18 hours of curing at 120° C., the sample is removed from the glass mold and postcured for another 30 minutes at 150 ° C., 105 minutes at 180° C., 30 minutes at 200° C., followed by 4 hours at 220° C.

EXAMPLE B

Blend of PT Resin With Epoxy Novolac Resin

About 200 parts of a PT-30 resin (Component A) and about 200 parts of an epoxy novolac resin (Component F) are combined in a 500 ml beaker, which was heated in the same manner and under the same conditions described in Example A. About 0.21611 parts of the catalytic solution of Example A was added thereto, then the resulting mixture is degassed and molded in the manner described in Example A. After 18 hours of curing at 120° C., the sample was removed from the glass mold and post cured for another 0.5 hr at 150° C., 2 hours at 180° C., 0.5 hours at 200° C., followed by 4 hours at 220° C.

EXAMPLE C

Blend of PT Resin With Bis-A Type Epoxy Resin

About 174.9 parts of a PT-30 resin (Component A) and about 174.9 parts of a Bisphenol-A type epoxy resin (Component G) are combined in a 500 ml beaker, which is heated in the same manner and under the same conditions described in Example A. About 0.20351 parts of the catalytic solution of Example A is added thereto in the manner described in Example A. The resulting mixture is molded and cured in the manner described in Example A.

Comparative Example A

The PT resin of Example A is replaced with about 47 parts of the Bisphenol-A dicyanate of Comparative Example 1. Then, 53 parts of a tetrafunctional epoxy resin (Component E) is added thereto according to the method described in Shimp et al., "Co-Reaction of Epoxide and Cyanate Resins," 33rd Int'l SAMPE Symposium and Exhibition 1–13 ( California Mar. 7–10,1988).

Comparative Example C

The PT resin of Example C is replaced with about 57 parts of the Bisphenol-A dicyanate of Comparative Example 1. Then, 43 parts of an epoxy resin (Component G) is added thereto according to the method described in Shimp, "AroCy® Cyanate Ester Resins Chemistry, Properties & Applications, (3rd Edition, May 1991).

The thermal, electrical, and moisture absorption properties of the blends described in Examples A, B, and C and Comparative Examples A and C are illustrated in Table IV.

TABLE IV

| | Ex. A | Comp. Ex. A | Ex. B | Ex. C | Comp. Ex. C |
|---|---|---|---|---|---|
| Cure Temp., ° C. | 220 | 235 | 220 | 220 | 200 |
| Properties | | | | | |
| HDT, ° C. | | 237 | | | 190 |
| Tg (DMA), ° C. | 273.7 | | 216.7 | 221.6 | |
| Tg (TMA), ° C. | 291.3 | | 185.8 | 263.4 | |
| Flexural Strength, ASTM D790 | | | | | |
| MSI | 13.11 | 10.6 | 12.58 | 18.21 | 19.10 |
| (MPa) | (90) | (73) | (87) | (126) | (132) |
| Flexural Modulus, MSI | 0.56 | 0.44 | 0.55 | 0.53 | 0.40 |
| (GPa) | (3.9) | (3.0) | (3.8) | (3.7) | (2.8) |
| Elongation, % | 2.4 | 2.1 | 2.4 | 3.81 | 5.3 |
| Dielectric Constant @ 1 MHz | 3.39 | 3.3 | 3.0 | 3.17 | 3.1 |
| Dissipation Factor @ 1 MHz | 0.01814 | 0.017 | 0.01333 | 0.02463 | 0.013 |
| $H_2O$ Absorption, % (ASTM D570) | 0.47[a] | 2.1[b] | 0.36[a] | 0.32[b] | 1.2[a] |
| Compressive Strength, | | | | | |
| MSI | 49.19 | | 47.93 | 38.4 | |
| (MPa) | (339) | | (331) | (265) | |
| Compressive Modulus, | | | | | |
| MSI | 0.40 | | 0.38 | 0.35 | |
| (GPa) | (2.8) | | (2.6) | (2.4) | |

(a) Immersed in RT water for 24 hrs.
(b) Conditioned 64 hrs @ 92° C. and >95% RH "HDT", as used herein, refers to heat distortion temperature, which for purposes herein, is comparable to the glass transition temperature ("Tg"). It can be seen in Table IV. that the blend of the present invention has a higher Tg and an improved water absorption than those of the prior art dicyanate ester-epoxy blends. This is because the multicyanated esters of the present invention possess greater than two cyanate groups, which results in blends having a greater percentage of cured bonds and thus upon subsequent reaction, a greater percentage of triazines. The presence of a large amount of triazines contributes to a higher Tg and a lower water absorption.

We claim:

1. A blend comprising, based upon the total weight of the blend, a) from about 15 percent to about 50 percent of a multifunctional phenolic cyanate/phenolic triazine copolymer comprising three or more phenolic moieties of formula I:

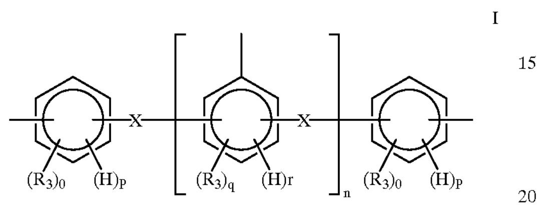

linked by way of at least one of open valences to one or more triazine moieties of the formula II:

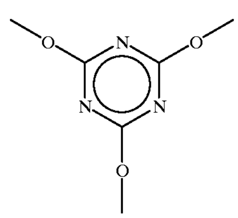

and wherein the remainder of the open valences of said phenolic moieties are substituted with —OH, —OCN, or other triazine moieties, provided that at least one of said remaining open valences is substituted with a —OCN moiety; wherein:

n is about 3 to about 10;

from, based upon the total moles of phenyl groups in said copolymer, about 5 to about 20 percent of the phenyl groups of said copolymer are substituted with —OCN groups and from about 5 to about 20 percent of said phenyl groups are substituted with —OH groups;

q is 0;

o is 0;

X is a moiety selected from the group consisting of —$OH_2$—, —$CF_2$—;

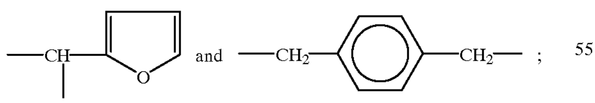

r is 3;

and p is 4; and $R_2$ and $R_3$ are the same or different at each occurrence and are a substituent other than hydrogen which is unreactive under conditions necessary to completely cure the copolymer; and b) from about 25 percent to about 70 percent of a brominated epoxy resin having the formula

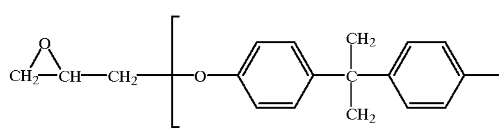

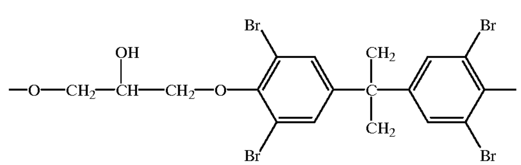

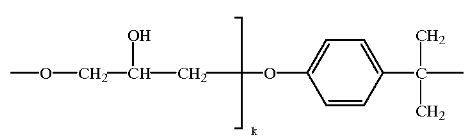

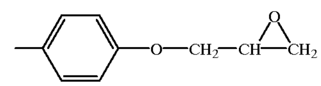

wherein k is from about 2 to about 3, said brominated epoxy resin comprising, based upon the total weight of said brominated epoxy resin, from about 50 percent to about 70 percent bromination;

c) from about 5 to about 10 percent of a tetrafunctional epoxy resin having the formula:

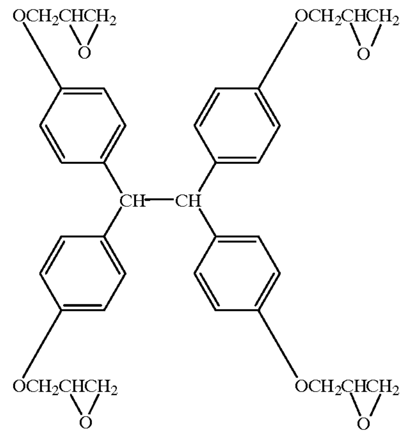

d) from about 0.01 percent to about 1 percent of a manganese octoate catalyst; and e) from about 0.5 percent to about 1 percent of a 2-methyl imidazol curing agent, said blend being curable whereby said tetrafunctional epoxy resin is crosslinked with said multifunctional phenolic cyanate/phenolic triazine copolymer, and said epoxy resin is crosslinked with said multifunctional phenolic cyanate/phenolic triazine copolymer.

2. A blend comprising, based upon the total weight of the blend, (a) from about 15 percent to about 50 percent of a multifunctional phenolic cyanate/phenolic triazine copolymer comprising three or more phenolic moieties of formula I:

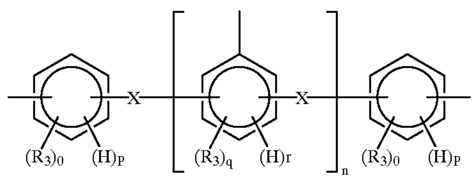

linked by way of at least one of open valences to one or more triazine moieties of the formula II:

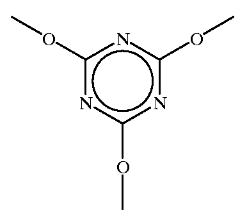

and wherein the remainder of the open valences of said phenolic moieties are substituted with —OH, —OCN, or other triazine moieties, provided that at least one of said remaining open valences is substituted with a —OCN moiety; wherein:

n is about 3 to about 10;

from, based upon the total moles of phenyl groups in said copolymer, about 5 to about 20 percent of the phenyl groups of said copolymer are substituted with —OCN groups and from about 5 to about 20 percent of said phenyl groups are substituted with —OH groups;

q is 0;

o is 0;

X is a moiety selected from the group consisting of $—CH_2—$, $—CF_2—$,

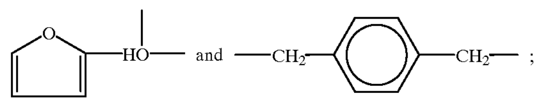

r is 3;

and p is 4; and $R_2$ and $R_3$ are the same or different at each occurrence and are substituent other than hydrogen which is unreactive under conditions necessary to completely cure the polymer; and (b) from about 25 percent to about 70 percent of an epoxy having the formula:

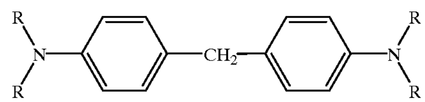

wherein R is

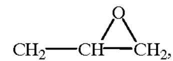

wherein said blend, upon being cured, has a glass transition temperature of at least about 200° C. (392° F.) and a water absorption rate of about 0.32 percent water after 24 hours immersion at room temperature;

blended with at least one catalyst selected from the group consisting of lead naphthenate, manganese naphthenate, manganese octoate, manganic acetylacetonate, cobalt octoate, cobalt naphthenate, cobalt acetylacetonate, zinc octoate, zinc naphthenate, zinc acetylacetonate, copper acetylacetonate, cupric naphthenate, nickel acetylacetonate, titanyl acetylacetonate, ferric octoate, tin octoate, diazobicyclo[2.2.2]-octane, catechol, 1,1-dimethyl-3-phenylurea, nonylphenole, 1-methylimidazole, 2-ethyl-4-methylimidazole, 2-phenylimidazole, and 2-methylimidazole, said blend being curable wherein said epoxy resin (b) is crosslinked with said multifunctional phenolic cyanate/phenolic triazine copolymer

3. A blend comprising:

(a) a multifunctional phenolic cyanate/phenolic triazine copolymer comprising three or more phenolic moieties of formula I:

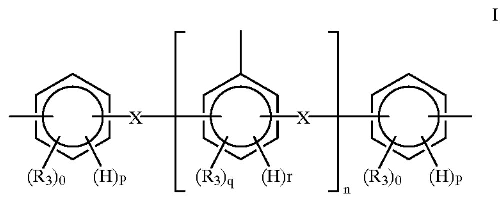

linked by way of at least one of open valences to one or more triazine moieties of the formula II:

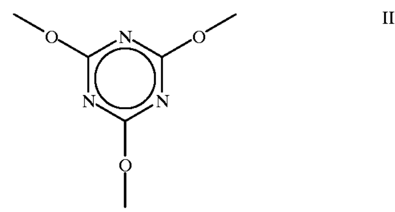

and wherein the remainder of the open valences of said phenolic moieties are substituted with —OH, —OCN, or other triazine moieties, provided that at least one of said remaining open valences is substituted with a —OCN moiety, wherein:

n is a positive whole number equal to or greater than 1, q and r are the same or different at each occurrence and are whole numbers from 0 to 3 with the proviso that the sum of q and r at each occurrence is equal to 3, o and p are the same or different at each occurrence and are whole numbers from 0 to 4, with the proviso that the sum of o and p is equal to 4, —X— is a divalent organic radical; and $R_3$ is the same or different at each occurrence and is a substituent other than hydrogen which is unreactive under conditions necessary to completely cure the copolymer; and (b) an epoxy resin selected from the group consisting of bisphenol-A-based epoxy resins, halogenated epoxy resins, epoxy novolac resins, polyglycol epoxy resins, multifunctional epoxy resins, mixtures thereof and copolymers thereof, said blend comprising, based upon the total weight of the blend, from about 5 to about 95 weight percent of said multifunctional phenolic cyanate/phenolic triazine copolymer and from about 5 to about 95 percent of said epoxy resin;

blended with at least one catalyst selected from the group consisting of lead naphthenate, manganese naphthenate, manganese octoate, manganic acetylacetonate, cobalt octoate, cobalt naphthenate, cobalt acetylacetonate, zinc octoate, zinc naphthenate, zinc acetylacetonate, copper acetylacetonate, cupric naphthenate, nickel acetylacetonate, titanyl acetylacetonate, ferric octoate, tin octoate, diazobicyclo[2.2.2]octane, catechol, 1,1-dimethyl-3-phenylurea, nonylphenol, 1-methylimidazole, 2-ethyl-4-methylimidazole, 2-phenylimidazole, 2-methylimidazole, and mixtures thereof.

4. The blend as claimed in claim 3, wherein said blend comprises, based upon the total weight of the blend, from about 15 to about 50 percent of the multifunctional phenolic cyanate/phenolic triazine copolymer and from about 25 to about 70 percent of said epoxy resin, and the amount of phenol groups in said copolymer is, based upon the total mole percent of multifunctional phenolic cyanate/phenolic triazine copolymer, from about 2 to about 25 mole percent.

5. The blend as claimed in claim 3 wherein up to about 90 mole percent of the phenyl groups in said copolymer are substituted with —OCN groups, said mole content being based upon the total moles of phenyl groups in said copolymer.

6. The blend as claimed in claim 3 wherein X is substituted or unsubstituted methylene or 1,4-phenyl-dimethylene, wherein permissible substituents are alkyl having from 1 to about 10 carbon atoms, halogen, and furyl.

7. The blend as claimed in claim 3 wherein said multifunctional epoxy resin is a tetrafunctional epoxy resin which is:

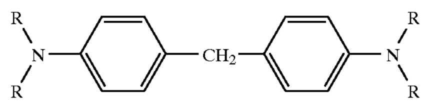

wherein R is

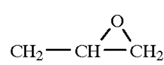

or

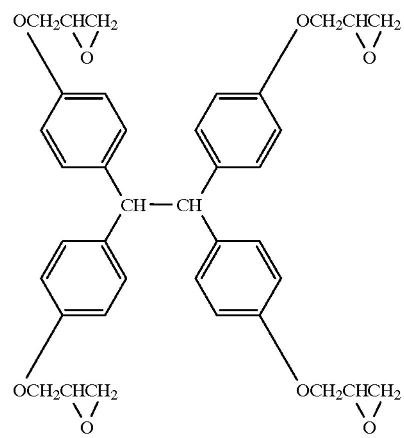

or is a trifunctional epoxy resin which is:

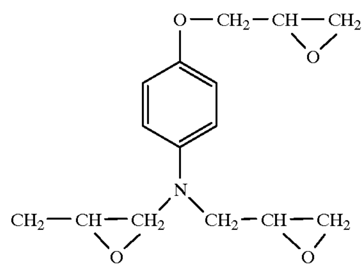

8. The blend as claimed in claim 7 wherein said tetrafunctional epoxy resin is crosslinked with said multifunctional phenolic cyanate/phenolic triazine copolymer, and said trifunctional epoxy resin is crosslinked with said multifunctional phenolic cyanate/phenolic triazine copolymer.

9. The blend as claimed in claim 3 wherein X is a moiety selected from the group consisting of:

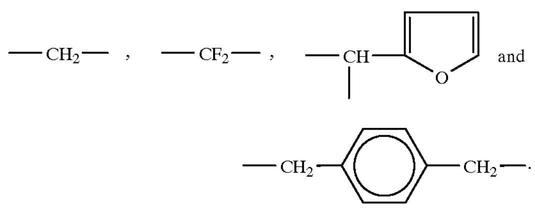

10. The blend as claimed in claim 3 wherein n is from about 1 to about 20.

11. The blend as claimed in claim 3 wherein:

o is 0 or 1;

p is 3 or 4;

q is 0 or 1; and r is2or 3.

12. The blend as claimed in claim 3 wherein $R_3$ is methyl or ethyl.

13. The blend as claimed in claim 3 wherein said halogenated epoxy has, based upon the total weight of the epoxy resin, from about 15 percent to about 45 percent halogenation.

14. The blend as claimed in claim 3 further comprising, based upon the total weight of the blend, from about 0.08 to about 0.11 percent of at least one catalyst.

15. The blend as claimed in claim 3 wherein said catalyst is selected from the group consisting of manganese octoate and 2-methyl imidazole.

16. The blend as claimed in claim 3 further comprising, based upon the total weight of the blend, up to about 20 percent of a multifunctional epoxy resin component which is different from the epoxy resin of component (b).

17. The blend as claimed in claim 16 wherein said epoxy resin (b) is crosslinked with said multifunctional phenolic cyanate/phenolic triazine copolymer, and said multifunctional epoxy resin which is different from said-epoxy resin (b) is crosslinked with said multifunctional phenolic cyanate/phenolic triazine copolymer.

18. The insulating substrate as claimed in claim 17 wherein said multifunctional epoxy which is different from said epoxy resin (b) is a tetrafunctional epoxy resin.

19. The blend as claimed in claim 3 which has a glass transition temperature of at least about 200° C. (392° F.) and a flexural strength of at least about 13 KSI (90 MPa).

20. The blend as claimed in claim 3 which has a flexural modulus of at least about 0.53 MSI (3.7 GPa) and a water absorption rate of about 0.32 percent water after 24 hours immersion at room temperature.

21. A blend comprising:

(a) a multifunctional phenolic cyanate/phenolic triazine copolymer comprising three or more phenolic moieties of formula I:

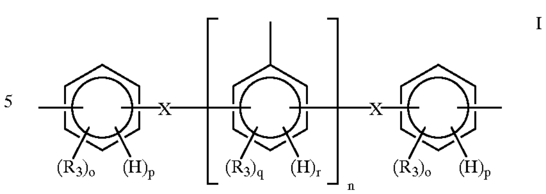

linked by way of at least one of open valences to one or more triazine moieties of the formula II:

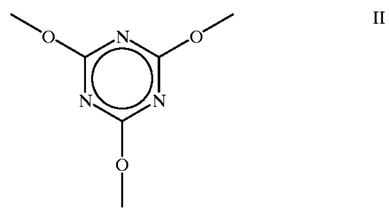

and wherein the remainder of the open valences of said phenolic moieties are substituted with —OH, —OCN, or other triazine moieties, provided that at least one of said remaining open valences is substituted with a —OCN moiety, wherein:

n is a positive whole number equal to or greater than 1, q and r are the same or different at each occurrence and are whole numbers from 0 to 3 with the proviso that the sum of q and r at each occurrence is equal to 3, o and p are the same or different at each occurrence and are whole numbers from 0 to 4, with the proviso that the sum of o and p is equal to 4, —X— is a divalent organic radical; and $R_3$ is the same or different at each occurrence and is a substituent other than hydrogen which is unreactive under conditions necessary to completely cure the copolymer; and (b) an epoxy resin selected from the group consisting of the compounds having the following formulas:

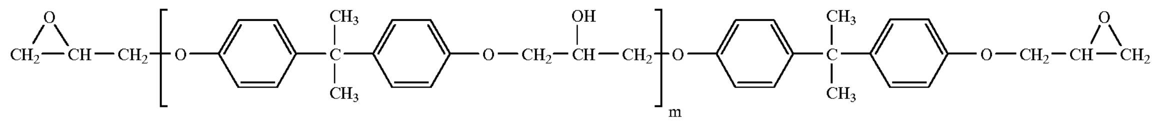

wherein m is from about 0.1 to about 1,

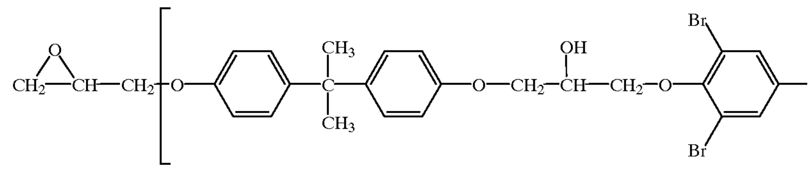

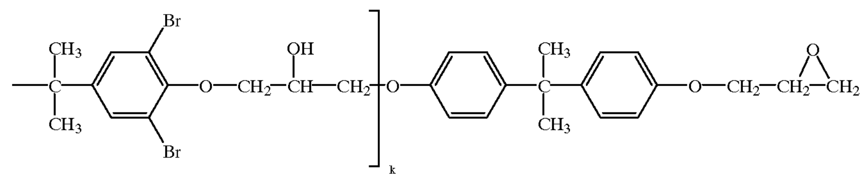

wherein k is from about 2 to about 3,

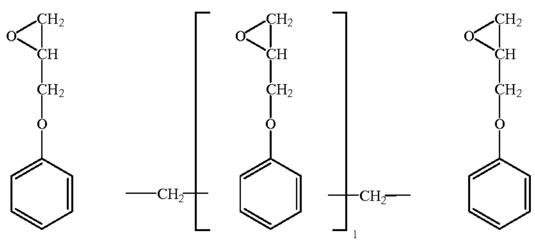

wherein I is from about 0.1 to about 2,

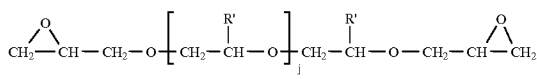

wherein j is from about 1 to about 2 and R' is an organic group or hydrogen, tetra-functional epoxy resins, tri-functional epoxy resins, mixtures thereof and combinations thereof, said blend comprising, based upon the total weight of the blend, from about 5 to about 95 weight percent of said multifunctional phenolic cyanate/phenolic triazine copolymer and from about 5 to about 95 weight percent of said epoxy resin;

blended with at least one catalyst selected from the group consisting of lead naphthenate, manganese naphthenate, manganese octoate, manganic acetylacetonate, cobalt octoate, cobalt naphthenate, cobalt acetylacetonate, zinc octoate, zinc naphthenate, zinc acetylacetonate, copper acetylacetonate, cupric naphthenate, nickel acetylacetonate, titanyl acetylacetonate, ferric octoate, tin octoate, diazobicyclo[2.2.2.]octane, catechol, 1,1-dimethyl-3-phenylurea, nonylphenol, 1-methylimidazole, 2-ethyl-4-methylimidazole, 2-phenylimidazole, 2-methylimidazole, and mixtures thereof.

22. The blend as claimed in claim 21 wherein the blend comprises, based upon the total weight of the blend, from about 15 to about 50 percent of the multifunctional phenolic cyanate/phenolic triazine copolymer and from about 25 to about 70 percent of said epoxy resin, and the amount of phenol groups in said copolymer is, based upon the total mole percent of multifunctional phenolic cyanate/phenolic triazine copolymer, from about 2 to about 25 mole percent.

23. The blend as claimed in claim 21 wherein up to about 90 mole percent of the phenyl groups in said copolymer are substituted with —OCN groups, said mole content being based on the total moles of phenol groups in said copolymer.

24. The blend as claimed in claim 21 wherein X is substituted or unsubstituted methylene or 1,4-phenyl-dimethylene, wherein permissible substituents are alkyl having from 1 to about 10 carbon atoms, halogen, and furyl, n is from about 1 to about 20, o is 0 or 1, p is 3 or 4,q is 0 or 1, r is 2 or 3, and $R_3$ is methyl or ethyl.

25. The blend as claimed in claim 21 wherein, based upon the total weight of the blend, from about 0.01 to about 1 percent of said at least one catalyst is present.

26. The blend as claimed in claim 21 further comprising, based upon the total weight of the blend, from about 0.01 to about 1 percent of the curing agent.

27. The blend as claimed in claim 21 further comprising, based upon the total weight of the blend, up to about 20 percent of a multifunctional epoxy resin component in addition to the epoxy resin of component b.

28. The blend as claimed in claim 27 wherein said epoxy resin (b) is crosslinked with said multifunctional phenolic cyanate/phenolic triazine copolymer, and said multifunctional epoxy resin which is different from said epoxy resin (b) is crosslinked with said multifunctional phenolic cyanate/phenolic triazine copolymer.

29. The insulating substrate as claimed in claim 28 wherein said multifunctional epoxy which is different from said epoxy resin (b) is a tetrafunctional epoxy resin.

30. The blend as claimed in claim 21 which has a glass transition temperature of at least about 200° C. (392° F.) and a flexural strength of at least about 13 KSI (90 MPa).

31. The bland as claimed in claim 21 which has a flexural modulus of at least about 0.53 MSI (3.7 GPa) and a water absorption rate of about 0.32 percent water after 24 hours immersion at room temperature.

* * * * *